US00PP32179P2

(12) United States Plant Patent
Koot

(10) Patent No.: US PP32,179 P2
(45) Date of Patent: Sep. 8, 2020

(54) ***PORTULACA* PLANT NAMED 'DOPORTCUPCOCON'**

(50) Latin Name: *Portulaca hybrida*
Varietal Denomination: Doportcupcocon

(71) Applicant: DUMMEN GROUP B.V., De Lier (NL)

(72) Inventor: Arjan Koot, Oeffelt (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 16/602,352

(22) Filed: Sep. 23, 2019

(51) Int. Cl.
*A01H 5/02* (2018.01)

(52) U.S. Cl.
USPC ..... Plt./471

(58) Field of Classification Search
USPC ..... Plt./471
CPC ..... A01H 5/02
See application file for complete search history.

(56) References Cited

PUBLICATIONS

PLUTO Plant Variety Database Mar. 26, 2020. p. 1.*

* cited by examiner

*Primary Examiner* — Annette H Para
(74) *Attorney, Agent, or Firm* — C. A. Whealy

(57) ABSTRACT

A new and distinct cultivar of *Portulaca* plant named 'Doportcupcocon', characterized by its compact and spreading to prostrate growth habit; vigorous growth habit; freely branching habit; freely flowering habit; large white-colored flowers; and good garden performance.

2 Drawing Sheets

Figure 1:
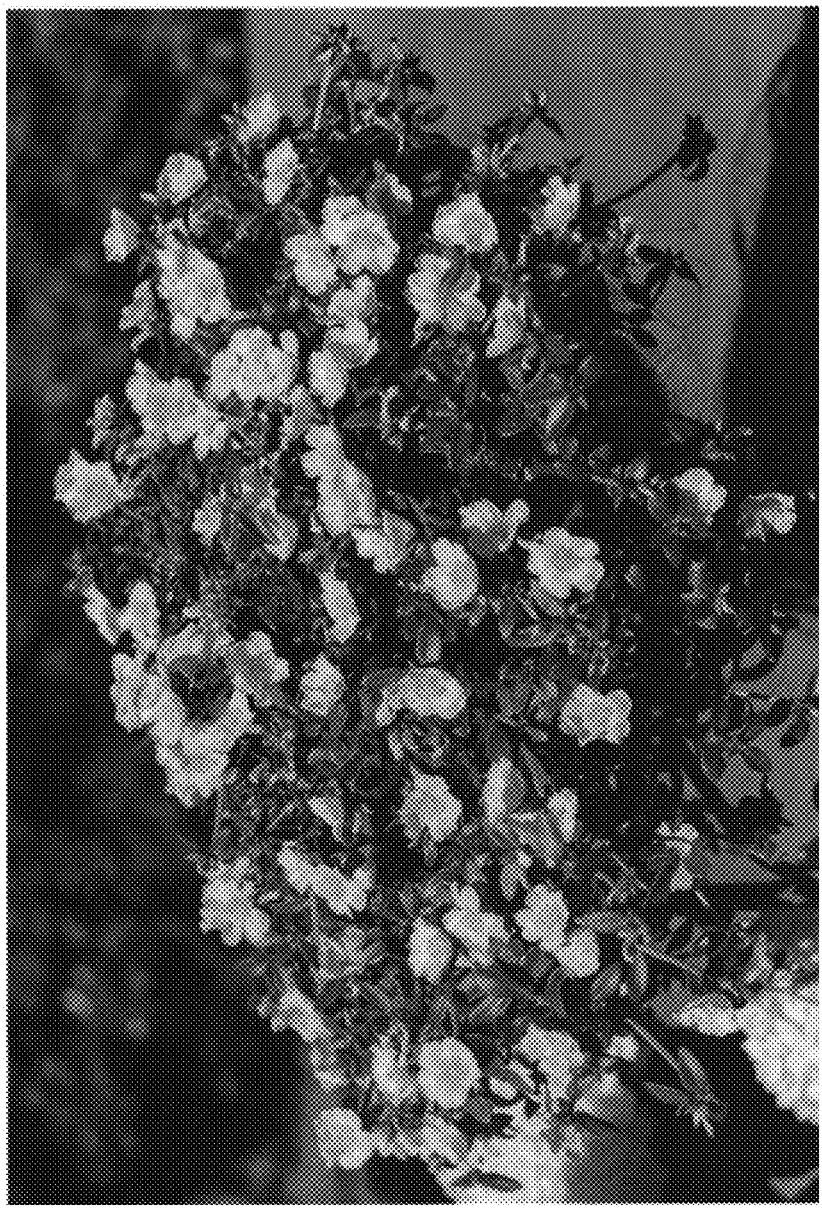

Botanical designation: *Portulaca hybrida.*
Cultivar denomination: 'DOPORTCUPCOCON'.

BACKGROUND OF THE INVENTION

The present invention relates to a new and distinct cultivar of *Portulaca* plant, botanically known as *Portulaca hybrida* and hereinafter referred to by the name 'Doportcupcocon'.

The new *Portulaca* plant is a product of a planned breeding program conducted by the Inventor in Rheinberg, Germany. The objective of the breeding program is to create new spreading *Portulaca* plants with numerous large and attractive flowers.

The new *Portulaca* plant originated from a cross-pollination made by the Inventor in Rheinberg, Germany in July, 2016 of a proprietary selection of *Portulaca hybrida* identified as code number RR13-001015-001, not patented, as the female, or seed, parent with a proprietary selection of *Portulaca hybrida* identified as code number RR15-001110-002, not patented, as the male, or pollen, parent. The new *Portulaca* plant was discovered and selected by the Inventor as a flowering plant from within the progeny of the stated cross-pollination in a controlled greenhouse environment in Rheinberg, Germany in May, 2018.

Asexual reproduction of the new *Portulaca* plant by vegetative terminal cuttings in a controlled greenhouse environment in Rheinberg, Germany since June, 2018, has shown that the unique features of this new *Portulaca* plant are stable and reproduced true to type in successive generations.

SUMMARY OF THE INVENTION

Plants of the new *Portulaca* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'Doportcupcocon'. These characteristics in combination distinguish 'Doportcupcocon' as a new and distinct *Portulaca* plant:

1. Compact and spreading to prostrate growth habit.
2. Vigorous growth habit.
3. Freely branching habit.
4. Freely flowering habit.
5. Large white-colored flowers.
6. Good garden performance.

Plants of the new *Portulaca* can be compared to plants of the female parent selection. Plants of the new *Portulaca* differ primarily from plants of the female parent selection in the following characteristics:

1. Plants of the new *Portulaca* flower earlier than plants of the female parent selection.
2. Plants of the new *Portulaca* have larger flowers than plants of the female parent selection.

Plants of the new *Portulaca* can be compared to plants of the male parent selection. Plants of the new *Portulaca* differ primarily from plants of the male parent selection in flower color as plants of the new *Portulaca* have white-colored flowers whereas plants of the male parent selection have creamy white-colored flowers.

Plants of the new *Portulaca* also can be compared to plants of the *Portulaca hybrida* 'Duna White', not patented. In side-by-side comparisons, plants of the new *Portulaca* differ primarily from plants of 'Duna White' in the following characteristics:

1. Plants of the new *Portulaca* are more compact than plants of 'Duna White'.

2. Plants of the new *Portulaca* have lighter green-colored leaves than plants of 'Duna White'.
3. Flowers of plants of the new *Portulaca* have more stamens than flowers of plants of 'Duna White'.

BRIEF DESCRIPTION OF THE PHOTOGRAPHS

The accompanying colored photographs illustrate the overall appearance of the new *Portulaca* plant showing the colors as true as it is reasonably possible to obtain in colored reproductions of this type. Colors in the photographs may differ slightly from the color values cited in the detailed botanical description which accurately describe the colors of the new *Portulaca* plant.

The photograph on the first sheet (FIG. 1 of 2) is a side perspective view of a typical flowering plant of 'Doportcupcocon' grown in a container.

Figure 2:
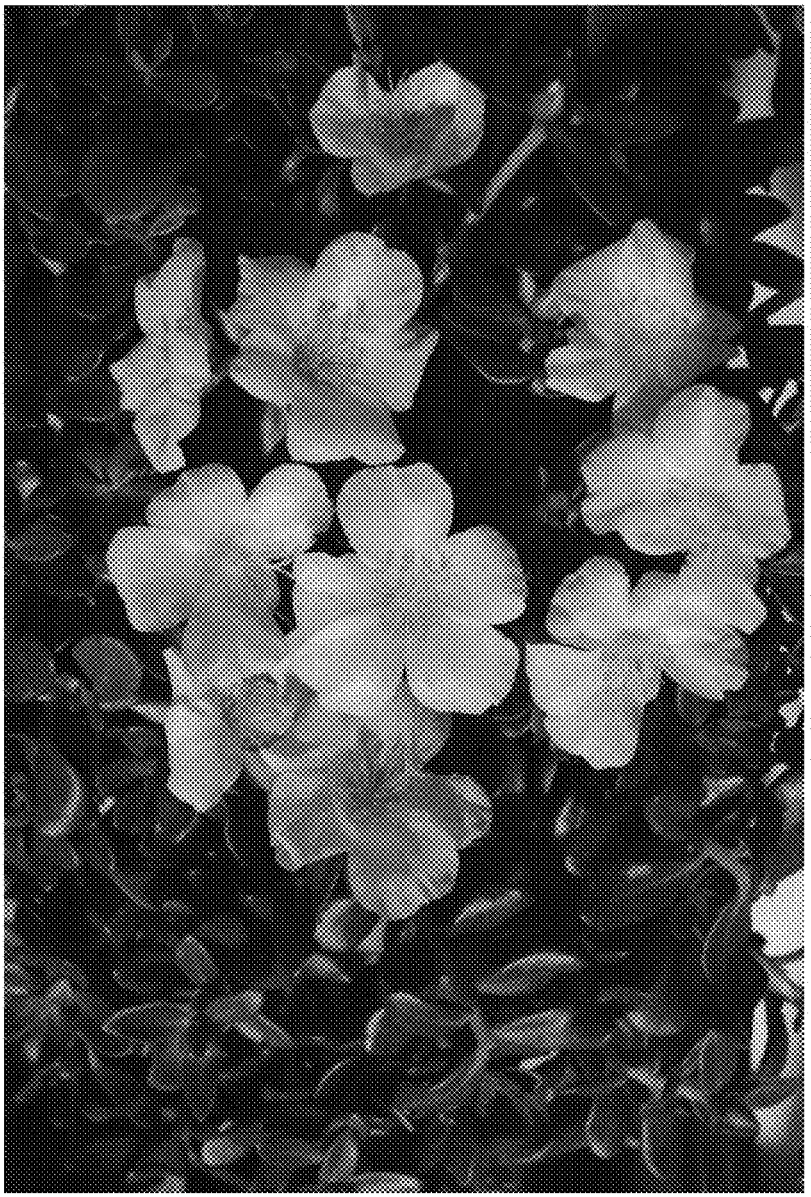

The photograph on the second sheet (FIG. 2 of 2) is a close-up view of a typical flowering plant of 'Doportcupcocon'.

DETAILED BOTANICAL DESCRIPTION

The aforementioned photographs and following observations, measurements and values describe plants grown during the spring and summer in 13-cm containers in a glass-covered greenhouse in Rheinberg, Germany and under cultural practices typical of commercial *Portulaca* production. During the production of the plants, day and night temperatures averaged 18° C. and light levels averaged 1,500 lux. Plants were pinched one time three weeks after planting and were twelve weeks old when the photographs and the description were taken. In the description, color references are made to The Royal Horticultural Society Colour Chart, Fifth Edition, except where general terms of ordinary dictionary significance are used.

Botanical classification: *Portulaca hybrida* 'Doportcupcocon'.

Parentage:

*Female, or seed, parent*.—Proprietary selection of *Portulaca hybrida* identified as code number RR13-001015-001, not patented.

*Male or pollen parent*.—Proprietary selection of *Portulaca hybrida* identified as code number RR15-001110-002, not patented.

Propagation:

*Type*.—By vegetative terminal cuttings.

*Time to initiate roots, summer*.—About five days at temperatures about 20° C.

*Time to initiate roots, winter*.—About seven days at temperatures about 20° C.

*Time to produce a rooted young plant, summer*.—About three weeks at temperatures about 20° C.

*Time to produce a rooted young plant, winter*.—About four weeks at temperatures about 20° C.

*Root description*.—Fine, fibrous; close to 159C in color, actual color of the roots is dependent on substrate composition, water quality, fertilizers, substrate temperature and age of roots.

*Rooting habit*.—Freely branching; dense.

Plant description:

*Plant and growth habit*.—Compact and spreading to prostrate plant habit; vigorous growth habit; moderate growth rate.

*Branching habit*.—Freely branching habit about ten primary lateral branches each with about six to eight secondary lateral branches developing per plant; pinching enhances branching potential.

*Plant height, soil level to top of foliar plane*.—About 15 cm.

*Plant height, soil level to top of floral plane*.—About 15 cm.

*Plant diameter* (*area of spread*).—About 25 cm.

Lateral branch description:

*Length*.—About 20 cm.

*Diameter*.—About 6 mm.

*Internode length*.—About 1.8 cm.

*Strength*.—Moderately strong, flexible.

*Texture and luster*.—Smooth, glabrous; glossy.

*Color, developing and developed*.—Close to 145A.

Leaf description:

*Arrangement*.—Alternate, simple.

*Length*.—About 2.5 cm.

*Width*.—About 1.1 cm.

*Shape, developing leaves*.—Elliptic.

*Shape, fully expanded leaves*.—Obovate.

*Apex*.—Cuspidate.

*Base*.—Attenuate.

*Margin*.—Entire.

*Texture and luster, upper and lower surfaces*.—Smooth, glabrous; fleshy, succulent; glossy.

*Venation pattern*.—Pinnate.

*Color*.—Developing leaves, upper surface: Close to 137B to 137C. Developing leaves, lower surface: Close to 138B. Fully expanded leaves, upper surface: Close to 137D; venation, close to 137D. Fully expanded leaves, lower surface: Close to 138C; venation, close to 138B.

*Petioles*.—Length: About 3 mm. Diameter: About 2.8 mm. Texture and luster, upper and lower surfaces: Smooth, glabrous; semi-glossy. Strength: Moderately strong. Color, upper and lower surfaces: Close to 145B.

Flower description:

*Flower arrangement*.—Single rotate flowers; freely flowering habit with 60 open flowers and flower buds per plant at one time; flowers face mostly upright to outwardly.

*Fragrance*.—None detected.

*Natural flowering season*.—Plants begin flowering about twelve weeks after planting; in the garden, plants flower continuously from spring until autumn in Germany.

*Flower longevity*.—Flowers last about one day on the plant; flowers not persistent.

*Flower buds*.—Length: About 1 cm. Diameter: About 6 mm. Shape: Ovoid. Texture and luster: Smooth, glabrous; semi-glossy. Color: Close to 144C and 155B.

*Flower diameter*.—About 2.5 cm.

*Flower length* (*height*).—About 1.6 cm.

*Petals*.—Quantity per flower: Corolla consists of five petals fused at the base. Length: About 1.4 cm. Width: About 1.2 cm. Shape: Obovate. Apex: Emarginate. Base: Fused, truncate. Margin: Entire, slightly undulate. Texture and luster, upper and lower surfaces: Smooth, glabrous; glossy. Color: When opening and fully opened, upper surface: Close to 155C; venation, close to 155C; color does not change with development. When opening and fully opened, lower surface: Close to 155C; venation, close to 155C; color does not change with development.

*Sepals*.—Quantity per flower: Two fused into a tubular calyx. Length: About 8 mm. Width: About 5.5 mm. Shape: Ovate. Apex: Acuminate. Base: Fused, acute. Margin: Entire. Texture and luster, upper and lower surfaces: Smooth, glabrous; matte. Color, developing, upper and lower surfaces: Close to 145B. Color, fully developed, upper and lower surfaces: Close to 145B.

*Peduncles*.—Length: About 20 cm. Diameter: About 3.5 mm. Angle: Mostly upright to outwardly. Strength: Moderately strong, flexible. Texture and luster: Smooth, glabrous; semi-glossy. Color: Close to 145B.

*Reproductive organs*.—Androecium: Quantity of stamens per flower: About 93. Filament length: About 7 mm. Filament color: Close to 157A. Anther shape: Oval, bi-lobed. Anther length: About 1 mm. Anther color: Close to 17A. Amount of pollen: Abundant. Pollen color: Close to 23A. Gynoecium: Pistil length: About 1.5 cm. Style length: About 8 mm. Style color: Close to between 154D and 1D. Stigma diameter: About 7 mm. Stigma shape: Five-branched. Stigma color: Close to 155C. Ovary color: Close to 144A. Fruits: Quantity produced per plant: About 40 during the flowering season. Length: About 5 mm. Diameter: About 5.2 mm. Texture: Glabrous. Color: Close to 146D. Seeds: Quantity per flower: About 12 to 40. Length: About 1 mm. Diameter: About 1 mm. Texture: Smooth, glabrous. Color: Close to between 202B and N200B.

Garden performance: Plants of the new *Portulaca* have been observed to have good garden performance and to tolerate temperatures ranging from about 7° C. to about 35° C. and to be suitable for USDA Hardiness Zone 11.

Pathogen & pest resistance: To date, plants of the new *Portulaca* have not been shown to be resistant to pathogens and pests common to *Portulaca* plants.

It is claimed:

1. A new and distinct *Portulaca* plant named 'Doportcupcocon' as illustrated and described.

* * * * *